US010894970B2

(12) United States Patent
Bergel et al.

(10) Patent No.: US 10,894,970 B2
(45) Date of Patent: Jan. 19, 2021

(54) METHOD FOR SYNTHESISING ORGANIC MOLECULES

(71) Applicants: SUEZ GROUPE, Paris la Défense (FR); INSTITUT NATIONAL DE RECHERCHE EN SCIENCES ET TECHNOLOGIES POUR L'ENVIRONNEMENT ET L'AGRICULTURE, Antony (FR); CENTRE NATIONAL DE LA RECHERCHE SCIENTIFIQUE, Paris (FR); INSTITUT NATIONAL POLYTECHNIQUE, Toulouse (FR)

(72) Inventors: Alain Bergel, Toulouse (FR); Elise Blanchet, Bourg-Saint-Bernard (FR); Benjamin Erable, Giroussens (FR); Luc Etcheverry, Montlaur (FR); Yan Rafrafi, Castanet Tolosan (FR); Théodore Bouchez, Villemoisson (FR); Alain Huyard, Les Mureaux (FR)

(73) Assignees: SUEZ GROUPE, Paris la Défense (FR); INSTITUT NATIONAL DE RECHERCHE EN SCIENCES ET TECHNOLOGIES POUR L'ENVIRONNEMENT ET L'AGRICULTURE, Antony (FR); CENTRE NATIONAL DE LA RECHERCHE SCIENTIFIQUE, Paris (FR); INSTITUT NATIONAL POLYTECHNIQUE, Toulouse (FR)

( * ) Notice: Subject to any disclaimer, the term of this patent is extended or adjusted under 35 U.S.C. 154(b) by 137 days.

(21) Appl. No.: 16/063,599

(22) PCT Filed: Dec. 14, 2016

(86) PCT No.: PCT/EP2016/081050
§ 371 (c)(1),
(2) Date: Jun. 18, 2018

(87) PCT Pub. No.: WO2017/102871
PCT Pub. Date: Jun. 22, 2017

(65) Prior Publication Data
US 2019/0002932 A1 Jan. 3, 2019

(30) Foreign Application Priority Data
Dec. 18, 2015 (FR) ...................... 15 62789

(51) Int. Cl.
| | |
|---|---|
| *C12P 7/54* | (2006.01) |
| *C12P 7/04* | (2006.01) |
| *C25B 1/10* | (2006.01) |
| *C25B 15/08* | (2006.01) |
| *B01J 23/46* | (2006.01) |
| *B01J 23/745* | (2006.01) |
| *B01J 23/75* | (2006.01) |
| *B01J 23/755* | (2006.01) |
| *B01J 35/00* | (2006.01) |
| *B01J 35/06* | (2006.01) |
| *C12M 1/00* | (2006.01) |
| *C12P 7/40* | (2006.01) |

(52) U.S. Cl.
CPC .............. *C12P 7/54* (2013.01); *B01J 23/462* (2013.01); *B01J 23/745* (2013.01); *B01J 23/75* (2013.01); *B01J 23/755* (2013.01); *B01J 35/0033* (2013.01); *B01J 35/065* (2013.01); *C12M 29/00* (2013.01); *C12P 7/04* (2013.01); *C12P 7/40* (2013.01); *C25B 1/10* (2013.01); *C25B 15/08* (2013.01)

(58) Field of Classification Search
CPC combination set(s) only.
See application file for complete search history.

(56) References Cited

U.S. PATENT DOCUMENTS

| | | | |
|---|---|---|---|
| 6,881,759 | B2 | 4/2005 | Hojlund et al. |
| 2012/0288898 | A1 | 11/2012 | Lovley et al. |
| 2017/0322772 | A1 | 11/2017 | Abdallah |

FOREIGN PATENT DOCUMENTS

| | | |
|---|---|---|
| EP | 0 909 328 B1 | 4/1999 |
| WO | 98/00558 A1 | 1/1998 |
| WO | 2005/0005981 A2 | 1/2005 |
| WO | 2009131452 A1 | 10/2009 |
| WO | 2010/068994 A1 | 6/2010 |
| WO | 2011/056183 A1 | 5/2011 |
| WO | 2011/087821 A2 | 7/2011 |
| WO | 2014/043690 A1 | 3/2014 |
| WO | 2015/172972 A1 | 11/2015 |

OTHER PUBLICATIONS

Henstra et al: "Microbiology of synthesis gas fermentation for biofuel production", Current Opinion in Biotechnology, London, GB, vol. 18, No. 3, Jun. 8, 2007 (Jun. 8, 2007), pp. 200-206, XP022110181, ISSN: 0958-1669, DOI: 16.1016/J.COPBIO.2007.03.008.

Michael Köpke et al: "Fermentative production of ethanol from carbon monoxide", Current Opinion in Biotechnology, vol. 22, No. 3, Jun. 1, 2011 (Jun. 1, 2011), pp. 320-325, XP055104855, ISSN: 0958-1669, DOI: 10.1016/j.copbio.2011.01.005.

Zhao T S et al: "A novel low-temperature methanol synthesis method from CO/H2/CO2 based on the synergistic effect between solid catalyst and homogeneous catalyst", Catalysis Today, Elsevier, NL, vol. 149, No. 1-2, Jan. 15, 2010 (Jan. 15, 2010), pp. 98-104, XP026815666, ISSN: 0920-5861, [retrieved on Aug. 18, 2009].

(Continued)

*Primary Examiner* — Heidi Reese
(74) *Attorney, Agent, or Firm* — Nixon & Vanderhye (57) ABSTRACT

Disclosed is a method for synthesising organic molecules from carbon-containing sources and dihydrogen, as well as a device for implementing the method. The method can make use of carbon-containing sources and/or dihydrogen from renewable resources.

18 Claims, 3 Drawing Sheets
(3 of 3 Drawing Sheet(s) Filed in Color)

(56) References Cited

OTHER PUBLICATIONS

FR Search Report, dated Sep. 16, 2016, from corresponding FR 1 562 789 application.
International Search Report, dated Mar. 20, 2017, from corresponding PCT/EP2016/081050 application.

METHOD FOR SYNTHESISING ORGANIC MOLECULES

BACKGROUND OF THE INVENTION

Field of the Invention

The present invention relates to a process for synthesising organic molecules from carbon and dihydrogen sources as well as a device able to implement said process. The process according to the invention can use carbon and/or dihydrogen sources from renewable resources.

The depletion of world fossil fuel resources and the increasing awareness of a possible anthropogenic effect on climate change result in increasingly reducing greenhouse effect gas emissions to develop a more sustainable society.

Economic, environmental and political impacts of petroleum-based economy have caused the development of processes which convert renewable products into fuel and chemicals which can replace petroleum-based products. Two important purposes of these development processes comprise cost competitiveness with petroleum-based processes and greenhouse effect gas emission reduction.

Description of the Related Art

One approach for achieving these purposes is the development processes for converting $H_2$ and $CO_2$ into chemical compounds that can be readily stored and transported as well as used as fuel or exploited in chemical synthesis industry. Thus, Williams R. et al. (Appl. Phys. Lett. 1978, 33, 381-383) describe the reversible of conversion $H_2$ and $CO_2$ into formate in order to be able to store hydrogen while avoiding related restrictions because of the explosive and diffusive hydrogen potential.

Many studies are concerned with implementing hydrogenation homogeneous or heterogeneous catalysis of $CO_2$ into organic molecules of interest. Thus, Moret S. et al. (Nat. Commun. 2014, 5, 4017-4023) describe a hydrogenation catalysis of $CO_2$ into formate whereas H. Li et al. (Science 2012, 335, 1596-1596) describe a hydrogenation catalysis of $CO_2$ into isobutanol and 3-methyl-1-butanol using *Ralstonia eutropha* H16, a genetically modified chemolithoautotrophic microorganism.

This microbial catalysis for the production of organic molecules of interest is a clear advantage since the microorganisms used offer a large $H_2$ and $CO_2$ conversion potential and in addition, the microorganisms are the proper catalysts of these catalytic reactions.

To date, microbial catalyses are essentially implemented with pure cultures and the use of microbial consortia is rare.

Biomass gasification leads to the production of synthesis gas (syngas) which is a key intermediate in the synthesis of synthetic fuels. This gas essentially consists of carbon monoxide and hydrogen molecules which act as building blocks in processes as the Fischer-Tropsch synthesis to form linear alkanes. Henstra A. M. et al. (*Curr Opin Biotechnol*, 2007, 18:1-7) is a review on fermentation of this synthesis gas by microorganisms which leads to the production of fuel and various chemicals like acetate, ethanol, butanol, butyrate and pure hydrogen.

Another approach consists in developing bioraffining processes using microorganisms to convert sources of renewable raw materials such as cellulosic biomass or waste into products which are traditionally petroleum-based or that can replace petroleum-based products. Because of an increasing competition between bioraffining and food consumption of grains such as maize and sugar, it is clear that bioproduction of fuels and chemicals will require the use of a wide range of alternative renewable raw materials.

Thus, patent EP0909328 describes a process for producing an organic acid, alcohol or hydrogen by fermentation of an exhaust gas from an industrial process, said exhaust gas containing CO and water or $CO_2$ and hydrogen; the process is implemented in the presence of an aqueous nutrient medium in a bioreactor with anaerobic bacteria capable of converting exhaust gas into one of the expected products.

Also, application WO2015172972 describes a process for producing organic compounds comprising contacting a mixed culture of acetogenic and non-acetogenic microorganisms, with oxygen and a carbon source. The acetogenic microorganisms convert the carbon source into acetate and/or ethanol whereas the non-acetogenic microorganisms metabolise acetate and/or ethanol into organic compounds.

To be applicable to the industrial scale, these processes for synthesising organic molecules from renewable carbon sources should be optimised as regards both implementation and kinetics and yield.

Another conversion pathway of renewable compounds into organic molecules of interest is microbial electrosynthesis. By "microbial electrosynthesis", it is intended the production of organic compounds by reducing at least one carbon source thanks to the action of electrochemically active microorganisms present in a cathodic compartment, coupled with an anodic compartment where the oxidation of oxidisable organic compounds (for example organic waste) is performed, also under the action of electrochemically active microorganisms. Such processes are well known to those skilled in the art and are in particular described in international application WO2010068994.

When the microorganisms are electrochemically active and that they interact with an anode (by transferring electrons to the anode), such an electrode is called a biological anode, bioanode, or microbial anode, and the microorganisms are described as anodophilic. On the other hand, when the microorganisms are electrochemically active and that they interact with a cathode (by accepting electrons from the cathode), such an electrode is designated as a biological cathode, biocathode, or microbial cathode, and the microorganisms are described as cathodophilic.

Thus, international application WO2010068994 describes a process for producing chemical compounds using a bio-electrochemical system consisting of an anode and a cathode separated from each other by a membrane. This electrochemical system provides reducing equivalents and $CO_2$, through oxidation reaction, at the anode, and reduction reaction, at the cathodes, to a culture of microorganisms enabling complex chemical compounds to be produced.

International application WO2011087821 relates to systems and processes for generating organic compounds by using $CO_2$ as a carbon source and an electric current as an energy source. The system according to application WO2011087821 comprises a reaction cell consisting of an anode and a cathode separated from each other by a permeable membrane.

International application WO2014043690 describes microbial electrosynthesis methods enabling biodegradable and renewable plastic materials to be produced by using electricity and $CO_2$.

Finally, international application WO2009131452 is concerned with a device comprising a bioanode, containing a substrate that can be electrochemically oxidised and other optional compounds, and a biocathode, containing a substrate that can be electrochemically reduced and other optional compounds. The bioanode and biocathode are electrically connected and have at their surface, a catalyst intended to the catalysis of the electrochemical conversion of the substrate.

Microbial electrosynthesis often requires the separation of the reaction medium into two anodic and cathodic compartments by means of a separator, in particular in order to improve selectivity and yield, and thus to fulfil health and/or food regulatory requirements which could demand that organic molecules produced at the cathode are very strictly isolated from oxidised organic waste at the cathode.

This separator arises technological problems because it has to separate the solutions in which the cathode and anode are dipped while ensuring as quickly as possible ion transfer, between both compartments.

SUMMARY OF THE INVENTION

Therefore, there is a need for processes enabling large scale synthesis of organic molecules to be performed by conversion of renewable compounds (for example captured $CO_2$ and dihydrogen produced by waste treatment processes or from green energies) into organic molecules of interest. In particular, there is a need for developing such processes enabling organic molecules to be produced with improved kinetics and yield. Advantageously, this process will fulfil health and/or food regulatory requirements for the molecules produced.

Incidentally, the inventors have surprisingly discovered that a catalytic process comprising contacting microorganisms with a solid catalyst, in the presence of a dihydrogen stream, could enable kinetics and yield of the synthesis of organic molecules from a carbon source to be significantly increased with respect to processes without solid catalyst in which the microorganisms are the single catalysts.

One object of the present invention is thus to provide a process for synthesising organic molecules from a carbon source and dihydrogen, with improved kinetics and yield with respect to the processes of prior art. The carbon source and dihydrogen stream can come from productions from renewable resources, without however problems of contact between the organic molecules produced and organic waste type renewable resources.

The process for synthesising organic molecules according to the invention comprises contacting, in an aqueous liquid medium, under anaerobic conditions, at least one source of anaerobic microorganisms, capable of catalysing the reduction of a carbon molecule by dihydrogen, with at least one hydrogen stream, in the presence of at least one carbon source and at least one solid catalyst.

In accordance with the present invention, by "microorganisms capable of catalysing the reduction of a carbon molecule by dihydrogen", it is meant any chemioorganotrophic or chemiolithotrophic cells using preexisting organic or mineral matter both as an energy source and a carbon source and having a reducing power, or in other words capable of transferring electrons to the carbon substrate in order to make their reduction easier. These are for example the cathodophilic microorganisms described in known microbial electrosynthesis processes.

Without wishing to be bound to any theory, the solid catalyst according to the invention could allow the attachment to its surface of dihydrogen molecules, microorganisms and possibly a carbon substrate to be hydrogenated thus making the global reaction easier.

The process of the invention can be simply implemented in a gas-liquid or gas-solid-liquid contactor, which is a basic technology of process industries, and in particular petroleum industries (for example, catalytic hydrogenations or oxygenations), and which is a perfectly controlled technology at a very large scale.

The process for synthesising organic molecules according to the invention does not mandatorily require the coexistence of several types of microorganisms with different mechanisms of action, for example being acetogenic and non-acetogenic. Molecules are directly synthesised from the feed by a dihydrogen stream and the carbon source, in the presence of the catalytic system according to the invention.

In accordance with the invention, the process can further comprise a step of recovering the organic molecules synthesised for their subsequent use.

Within the scope of the invention, by "aqueous liquid medium", it is meant any culture medium suitable for the microorganisms seeded in the contactor and comprises all the nutrient elements necessary for their proper development and thus promoting their metabolism. These media are well known to those skilled in the art who will be able to choose the medium depending on the microorganisms used and the organic molecules desired.

The sources of microorganisms of the process according to the invention can for example comprise the cathodophilic microorganisms described in known microbial electrosynthesis processes.

Thus, application WO2010/068994 discloses the use of *Cupriviavidus necator* (*Alcaligenes eutrophus* or *Ralstonia eutropha*) for the production of poly-beta-hydroxybutyrate (PHB) type biopolymers. Liou et al., (Int. Syst. Evol. Microbiol., 2005, 55, 2085-2091) disclose the use of *Clostridium carboxidivorans* sp nov for the production of acetate, ethanol, butyrate and butanol from carbon dioxide by microbial electrosynthesis. Application WO2011/087821 discloses the use of bacteria of the *Geobacter, sporomusa, Clostridium* and *Moorella* genera as cathodophilic microorganisms for the production of organic molecules by microbial electrosynthesis.

The processes according to the invention can also be implemented with microorganisms capable of being developed in an anaerobic medium with high salt concentrations (for example NaCl concentrations in the order of a few grams to tens grams per liter), for example of the *Geobacter, Vibrio, Bacillus, Halothermothrix, Halanaerobium, Halocella* genera. The microorganisms of the *Halobacterium, Selenihalanaerobacter, Methanomicrobiales* genera are generally adapted and can be developed in media having an even higher salinity.

The gas dihydrogen stream can be either a dihydrogen stream alone, or a mixture of dihydrogen with another gas such as for example a $CO_2/H_2$ mixture, or a $CO/H_2$ mixture. These mixtures can contain other gases necessary for the development of the microorganism used or a neutral gas for regulating partial pressures as $N_2$ for example.

Advantageously, $CO_2$ and CO can be used as a carbon source for the at least one source of microorganisms.

Within the scope of the invention, $CO_2$, or CO, and $H_2$ are present in proportions close to the stoichiometric ratio of the synthesised molecule desired. Those skilled in the art will be able to choose these proportions in view of their general knowledge.

In one advantageous embodiment of the invention, all or part of the dihydrogen stream comes from a microbial electrolysis comprising the oxidation of organic waste. Such processes are for example described in the application WO2005005981. They implement, in an electrochemical reactor comprising an anode, a cathode, and an aqueous medium containing anodophilic electroactive bacteria, capable of bio-oxidise an organic substrate, and to transfer electrons to the anode. Under the effect of the potential difference applied between the anode and the cathode, electrons produced by the oxidation of bio-oxidisable organic waste introduced in the aqueous medium are transferred to the cathode, where a dihydrogen release happens.

In particular, organic waste can be industrial, agricultural, and domestic wastewater or domestic, industrial, plant or animal origin waste.

Compared to known microbial electrosynthesis processes, where the separation of the oxidised organic waste and the molecule of interest produced is delicate, this particular embodiment of the invention makes it possible to fulfil to strict isolation requirements between the organic molecules of interest produced and organic waste.

Indeed, hydrogen can be produced from organic waste in a microbial electrolysis cell, the dihydrogen flow thus produced can be recovered and sent to feed a separated remote organic molecule synthesis reactor.

According to one advantageous embodiment of the invention, all or part of the dihydrogen stream comes from an anaerobic digestion of organic waste. This embodiment also enables the problem of separating organic waste from organic molecules produced to be solved, since the anaerobic digestion can be remote and separated from the production of organic molecules.

According to one advantageous embodiment of the invention, all or part of the dihydrogen current comes from water electrolysis. According to one particularly advantageous mode, this water electrolysis is made with generating power by sources of renewable energies, such as for example wind or solar energy, so as to absorb for example temporary production surplus.

According to one advantageous embodiment of the invention, all or part of the dihydrogen stream comprises a dihydrogen mixture produced by at least two of the dihydrogen production methods described below.

In accordance with the invention, the at least one carbon source is
  a. either in gas form and chosen from carbon monoxide and carbon dioxide,
  b. or in solution and chosen from solutions comprising carbonates, $C_1$-$C_8$ carboxylates, sugars, lactate, and mixtures thereof.

When the at least one carbon source is in the gas form and chosen from carbon monoxide and carbon dioxide, the processes according to the invention contribute to solving the problem of capture of these gases in the environment and use a renewable carbon source.

In the present invention, as an example of $C_1$-$C_8$ carboxylates: methanoate (or formate), acetate, butyrate, propionate, pentanoate, hexanoate (or caproate), heptanoate and octanoate can be mentioned.

In the present invention, as an example of carbonates: calcium carbonates, magnesium carbonates, potassium carbonates, sodium carbonates, iron carbonates, manganese carbonates and any other carbonate suitable in view of the knowledge of those skilled in the art can be mentioned.

In accordance with the invention, by sugar or carbon hydrate, it is meant in particular glucose, lactose and xylose, or any other sugar or carbon hydrate suitable in view of the knowledge of those skilled in the art.

By "mixtures thereof", it is meant mixtures of at least two or more of these different carbon sources.

The at least one solid catalyst according to the invention enables the dihydrogen molecules and microorganisms and possibly the carbon substrate to be hydrogenated to be attached at its surface. In accordance with the invention, it can be chosen from electrically conducting or semi-conductor materials.

Within the scope of the invention, by "conducting", it is meant any material capable of letting an electric current pass and/or transferring electrons between chemical or biological species adsorbed at its surface and by "semi-conductor", it is meant any material that can behave either as an electrical insulator either as a conductor, depending on the conditions under which it is placed. Exemplary semi-conductor materials are for example doped or non-doped silicon.

Advantageously, the at least one solid catalyst is chosen from a hydrogenation catalyst or a catalyst comprising carbon materials, or a mixture thereof.

In the present invention, by "carbon material", it is meant any material essentially consisting of carbon atoms. Said carbon materials can be chosen from carbon, graphite, graphene, carbon nanotubes, diamond or any other form of carbon material known to those skilled in the art.

The solid catalyst according to the invention is preferentially chosen from metal materials, that is consisting of a metal and an alloy or a mixture of metals (bulk catalyst) including oxides thereof, or comprising one or more metals attached to a support (supported catalyst).

The metals of the solid metal catalysts according to the invention are chosen in particular from iron, ruthenium, cobalt, nickel, chromium, platinum, palladium, rhodium, or a mixture thereof, including a mixture of oxides thereof. Iron, cobalt, nickel and ruthenium will be preferred, and more particularly iron.

Copper, zinc, chromium or aluminium can also be chosen, alone or in mixture, or in mixture with the abovementioned metals, for example cobalt-copper, or zinc-aluminium.

The solid catalyst can be:
  mild steel, or carbon steel, when iron is mixed with carbon materials, or
  stainless steel, when iron is mixed with nickel or chromium, including oxides thereof.

The mixtures used as a catalyst according to the invention can also be any other mixture able to be used as a solid catalyst suitable in view of the knowledge of those skilled in the art.

The organic molecules synthesised by the process according to the invention depend on the composition of said solid catalyst, the carbon source, as well as the at least one source of microorganisms. Examples are given in the table 1 that follows:

TABLE 1

| References | Microorganisms | Substrates | Molecules produced |
|---|---|---|---|
| D. D. Woods, Biochem. J. 1936, 30, 515-527 | *Echerischia Coli* | $H_2/CO_2$ | formate |

TABLE 1-continued

| References | Microorganisms | Substrates | Molecules produced |
|---|---|---|---|
| US 2012/0288898 Losley and Nevin | *Sporomusa ovata* (DSM 2662) *Sporomusa sphhaeroides* (DSM 2875) *Clostridium ljungdahlii* (DSM 13528) *Clostridium aceticum* (DSM 1496) *Moorella thermoacetica* (DSM 21394) *Acetobacterium woodii* (DSM 1030) | $H_2/CO_2$ (80/20) | acetate |
| F. Barbirato et al (1998) Industrial crops and products, 7, 2-3, pp 281-289 | *Klebsiella pneumniae* *Citrobacter freundii* *Enterobacter agglomerans* *Clostridium butyricum* *Clostridium butyricum* | glycerol distiller's stillage | 1,3 propanediol |
| US 2014/0322772 Angenent and Agler | Microorganisms or mixture of microorganisms | Ethanol + Volatile Fatty Acid | caproate, caprilate |
| WO 2010/068994 Rozendal and Rabaey | *Cupriviadus necator* (*Alcaligenes eutrophus* or *Ralstonia eutropha*) | $H_2/CO_2$ | Biopolymers, poly-beta-hydroxybutyrate (PHB) |
| Liou et al (2005) Int. Syst. Evol. Microbiol., 55, pp 2085-2091 | *Clostridium carboxidivorans* | $H_2/CO_2$ | acetate, ethanol, butyrate, butanol |
| WO 2011/087821 Lovley and Nevin | *Geobacter* *Sporomusa* *Clostridium* *Moorella* | CO2 | Chemical compounds with at least 2C |

According to one aspect of the invention, said solid catalyst is in the form of a grid, a plate or a three-dimensional or porous structure. Said three-dimensional or porous structure can consist of balls, granules, powder or a superposition of grids, drilled or extended plates or any other three-dimensional or porous structure known to those skilled in the art enabling the contact area to be increased with microorganisms, dihydrogen and the at least one carbon source.

According to one advantageous embodiment of the invention, the porous conducting material has a porosity higher than one micrometre, optimally from 50 to 5 000 μm, advantageously from 200 to 2 000 μm, and further advantageously from 1 000 to 2 000 μm to allow access to a maximum area for the microorganisms, and possibly for them to be attached, all or part, to be developed therein.

According to another particular embodiment of the invention, said solid catalyst is a metal membrane and said catalyst is the diffuser of at least one gas stream.

According to a particular aspect of the invention, the solid hydrogenation catalyst can act as a support to the at least one source of microorganisms, in which case it causes the formation of a biofilm.

In the present invention, by "biofilm", it is meant a more or less complex multicellular community, that can be symbiotic or not, of microorganisms, that can fully or partially adhere to the surface of said hydrogenation catalyst and adhering to each other.

According to the present invention, the source of microorganisms is chosen from the group comprising pure cultures, co-cultures, environmental inocula and complex microbial consortia.

For the purposes of the invention, the at least one source of microorganisms are anaerobic microorganisms, these possibly being strict anaerobic microorganisms or optional anaerobic microorganisms.

In the present invention, by "environmental inocula", it is meant any sample comprising living germs that are introduced in a medium favourable for multiplying or identifying said germs.

Advantageously, the environmental inocula according to the invention can be: domestic, industrial, plant or animal origin waste; loam; manure; soil; wastewater such as domestic, industrial wastewater or of any other origin, for example inocula from salt marshes.

According to one advantageous embodiment of the invention, said microorganisms can:
either come directly from the carbon source as it can be found in its environment, or
be added after sterilising the carbon source.

According to one advantageous embodiment of the invention, the source of microorganisms is added after sterilising the at least one carbon source thus enabling selectivity of the organic molecules produced to be ensured.

The synthesis process according to the invention enables complex organic molecules to be produced. Among these molecules, hydrocarbons, alcohols, carboxylic acids, for example carboxylates such as formate, acetate, caproate, dicarboxylic acids such as itaconic acid, hydroxylated carboxylic acids, for example alpha hydroxylated acids, such as glycolate, lactate, biopolymers, for example polyhydroxyalkanoates (PHA), for example poly-beta-hydroxybutyrate (PHB) can be mentioned.

The organic molecules produced by the processes according to the invention generally comprise between 1 and 12 carbon atoms, in particular between 2 and 10 carbon atoms, in particular between 4 and 8 carbon atoms.

The organic molecules produced can include short carbon chains, and include between 1 and 3, or between 2 and 6 carbon atoms.

The organic molecules produced can also include sufficiently long carbon chains to provide them with lubricating or surface active properties.

Advantageously, when said organic molecules are alcohols, the latter are preferably ethanol, methanol, butanol, isobutanol, 1,3 propanediol and 1,4 butanediol.

Advantageously, when said organic molecules are carboxylic acids, the latter generally include between 1 and 12 carbon atoms, or even between 2 and 10 carbon atoms, or between 4 and 8 carbon atoms, as for example methanoate (or formate), acetate, butyrate, succinate, propionate, pentanoate, hexanoate (or caproate), heptanoate, octanoate, nonanoate, decanoate and 2,5 furanedicarboxylic.

In one particular embodiment, the process according to the invention enables hydrocarbons to be produced through a microbial Fischer-Tropsch reaction, that is by $H_2$+CO fermentation (Henstra A M, et al. (2007), *Curr Opin Biotechnol* 18:1-7; Köpke M. et al. (2011), *Current Opinion in Biotechnol*, 22, 320-325).

The Fischer-Tropsch reaction involves the catalysis of carbon monoxide and hydrogen for converting them into hydrocarbons. In this chemical process, the most common solid hydrogenation catalysts are iron, cobalt or ruthenium, as well as nickel. The interest of the conversion is to produce synthetic crude oil from charcoal or gas.

The Ficher-Tropsch reaction is the following one:

$$(2n+1)H_2+nCO \rightarrow C_nH_{2n+2}+nH_2O.$$

In the processes according to the invention, n is an integer generally between 1 and 20, more particularly between 2 and 12, more particularly between 4 and 8.

Another aspect of the invention relates to a device able to implement the process according to the invention, said device comprising:
- means for feeding at least one gas stream comprising dihydrogen,
- at least one carbon source,
- at least one source of microorganisms,
- at least one means for contacting said at least one gas stream and said microorganisms, and
- a solid catalyst.

Advantageously, the device according to the invention contacts the gases and the solution using a dispersion device, a membrane contactor, or any other means known to those skilled in the art ensuring optimum gas rate to the solution. By "optimum transfer rate", it is meant a gas transfer rate as close as possible to the gas consumption rate by the microbial reaction.

BRIEF DESCRIPTION OF THE DRAWINGS

The file of this patent contains at least one drawing executed in color. Copies of this patent with color drawings will be provided by the Patent and Trademark Office upon request and payment of the necessary fee.

FIGS. 1 to 4 and the examples hereinafter illustrate the present invention.

FIG. 1 shows an experimental scheme of an embodiment of the device implementing the process according to the invention. The device is a closed gas-liquid-solid contactor in an anaerobic atmosphere and comprises: a container 100 having a hydrogen gas inlet ($H_2$) and $CO_2$, a gas diffuser 101 enabling the gas mixture to be diffused into the container 100, and a solid catalyst as a grid 102 dipped in the culture medium 103 allowing the microbial synthesis from the at least one carbon source entering the container 100 through the conduit 106 regulated by an inlet valve 107. Once the organic molecules are produced, they exit through a conduit 104 regulated by a valve 105 in order to recover them. In the top portion of the container 100, a conduit 108 discharging the gas diffused by the diffuser 101 and means for measuring pH and hydrogen content 109 are present.

FIG. 2 shows an experimental scheme of a particular embodiment of the device implementing the process according to the invention. The device comprises a microbial electrolysis compartment 201 and a gas-liquid-solid contactor 202. Said compartment 201 comprises, at the anode, an organic waste inlet through the conduit 203 acting as a substrate for anodophilic microorganisms 204 present as a biofilm and then the treated effluents exit through the conduit 205; at the cathode, the inflow of electrons ($e^-$) allows water electrolysis which provides the gas-liquid-solid contactor 202 with dihydrogen necessary for making the process according to the invention. The organic molecules produced are recovered at the outlet 206 of the gas-liquid-solid contactor 202.

DESCRIPTION OF THE PREFERRED EMBODIMENTS

Example 1: Synthesis of Formate and Acetate from $CO_2$ and $H_2$ Catalysed by an Inoculum of Salt Marsh and by Stainless Steel Four contactors are disposed along two parallel lines which each include two series connected contactors (the gas mixture from the first one is introduced into the second one). Each line is fed by a gas mixture $N_2/CO_2/H_2$ (40/10/50 volume) at a continuous flow rate of 6 mL·min$^{-1}$. For each line, the first contactor contains a solid hydrogenation catalyst as a grid of stainless steel 316 L of 98 cm$^2$ total net area, the second one does not contain a hydrogenation catalyst.

Each contactor contains 122 mL of culture medium comprised of KCl 0.1 g/L, $NH_4Cl$ 1.5 g/L, $NaHCO_3$ 2.5 g/L, $NaH_2PO_4$ 0.6 g/L, $CaCl_2$ 0.01 g/L, $MgCl_2$ 0.1 g/L, NaCl 45 g/L, a mixture of vitamins (ATCC), 10 ml/L, mineral traces (ATCC) 10 ml/L. Each contactor is inoculated at 10% (v/v) by sediments of freshly harvested salt marsh from Gruissan salt marshes. 1 mM ammonium sulphate has been added in both contactors of the second line to attempt to promote development of sulphate reducing bacteria.

All the contactors are placed in a water bath the temperature of which is regulated at 30° C. Samplings are performed daily and analysed by HPLC.

The formation of formate is observed (FIG. 3) with, at the end of eight days, maximum concentrations of 415±40 mg·L$^{-1}$ in the presence of a grid and 275±5 mg·L$^{-1}$ in the absence of a hydrogenation catalyst as a grid. The addition of sulphate had no effect. However, the catalyst increases the final formate concentration by more than 50% as compared to that obtained in the absence of a grid.

Figure 1:
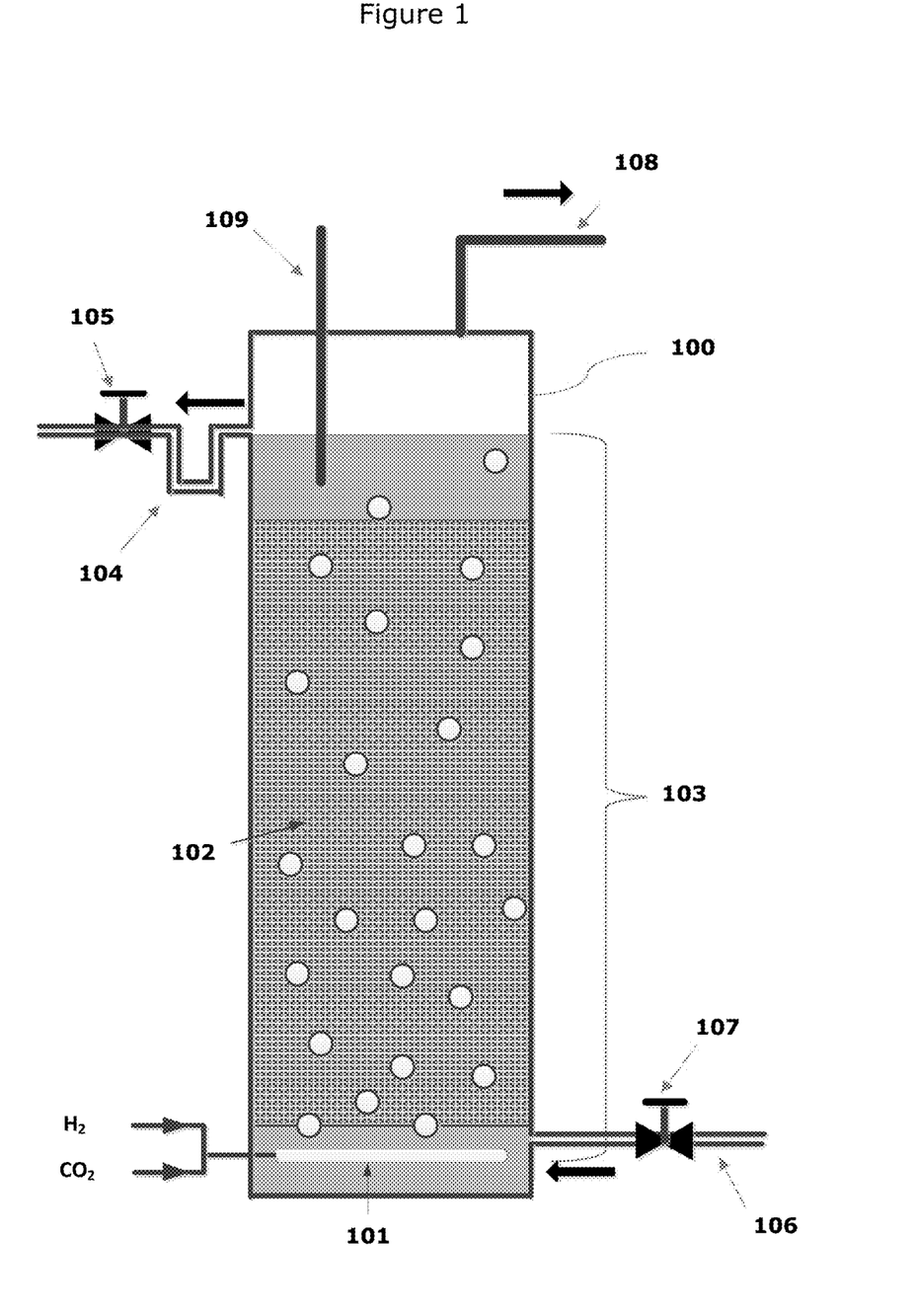
Figure 2:
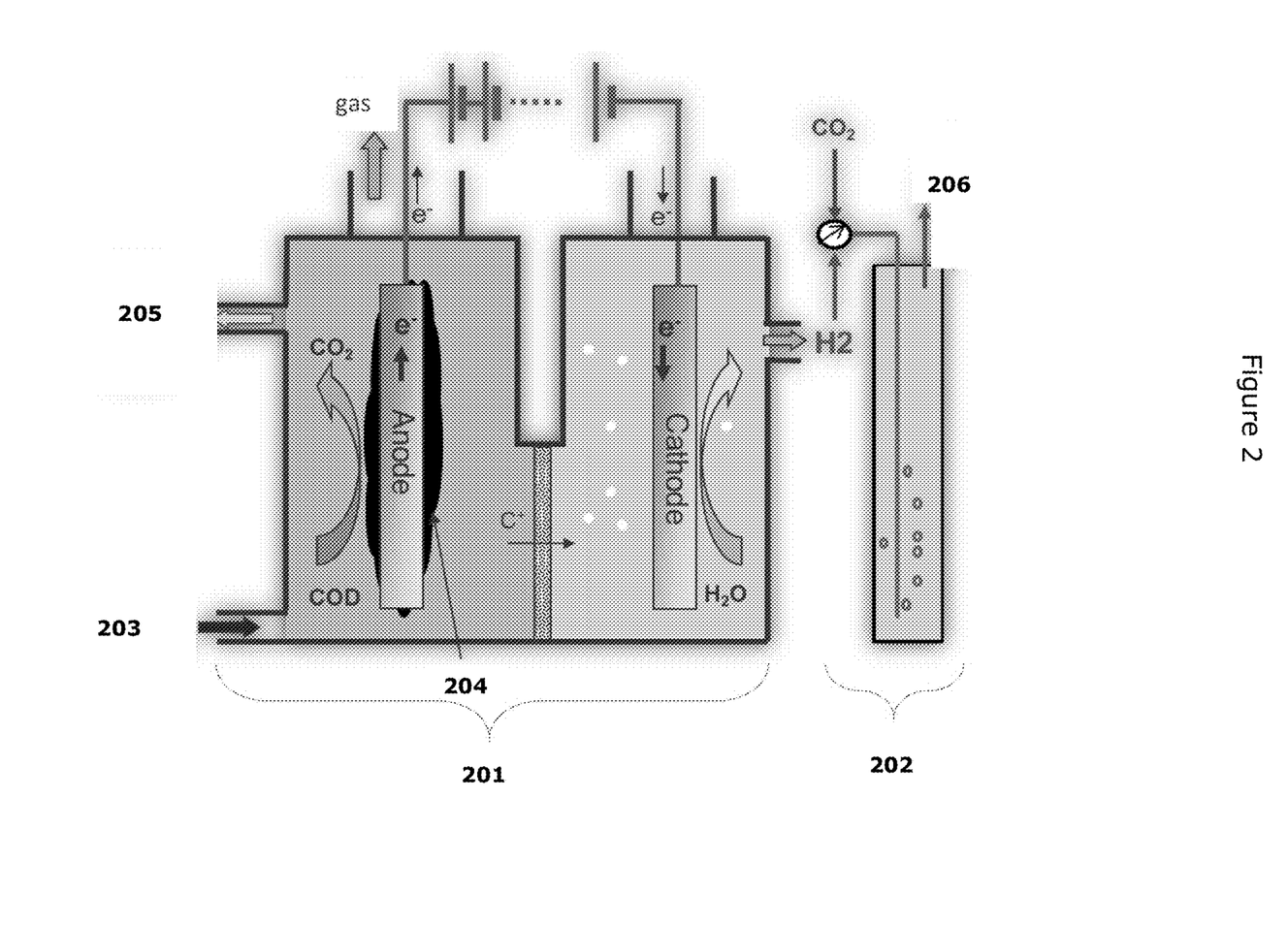
Figure 3:
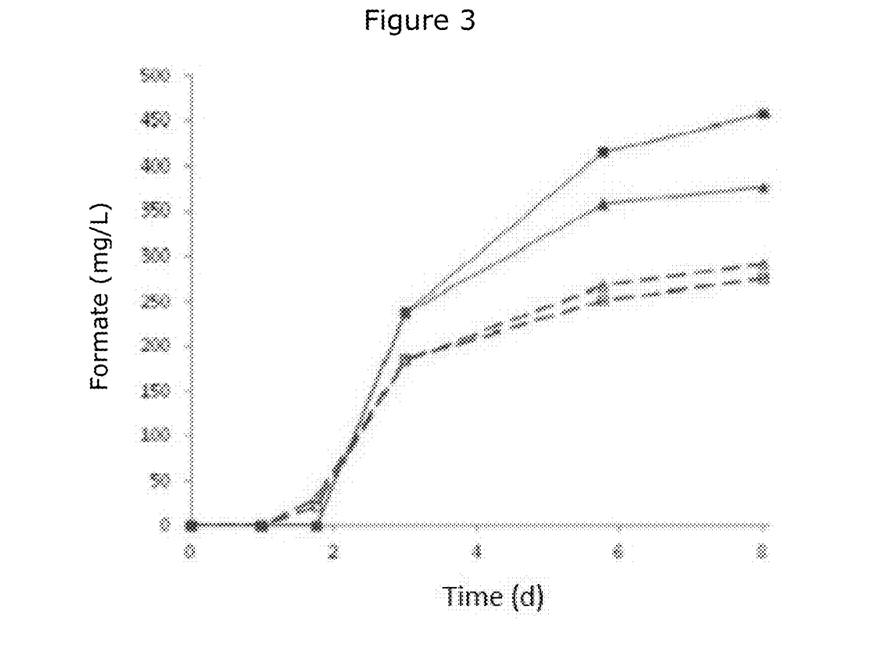
FIG. 3 represents the production of formate for 8 days in contactors inoculated by salt marshes and continuously fed by $N_2/CO_2/H_2$ (40/10/50 volume) in accordance with example 1. Said inoculated contactors are put either in the presence of a solid hydrogenation catalyst as a grid with sulphate (▲) or without sulphate (■), or in the absence of hydrogenation catalyst with sulphate (△) or without sulphate (□).

The presence of a hydrogenation catalyst as a stainless grid (solid curves) has a significant effect on the production with respect to controls made without a hydrogenation catalyst (dotted lines). The addition of sulphate (noted $SO_4$) has no significant effect.

Example 2: Synthesis of Acetate from $CO_2$ and $H_2$ Catalysed by a Sludge Inoculum of Purification Plant and by Stainless Steel The experimental device is similar to the previous one with a gas flow rate set to 18 mL·min$^{-1}$ and grids having total areas of 300 cm² in each contactor in question. They are washed beforehand in an ethanol:acetone (50:50) mixture and then stripped in a fluoro-nitric mixture. Each contactor is seeded with sludge of purification plant (PP) at a rate of 10% (v/v) in the culture medium comprised of: KCl 0.1 g/L, NH$_4$Cl 1.5 g/L, NaHCO$_3$ 2.5 g/L, NaH$_2$PO$_4$ 0.6 g/L, vitamins (ATCC) 10 mL/L, mineral trace (ATCC) 10 mL/L.

Finally, to limit the acetate consumption produced by the methanogenic bacteria which could be present in the consortium (according to the reaction CH$_3$COOH→CH$_4$+CO$_2$), the specific methanogenic inhibitor 2-bromoethanesulphonate (BES) is added at the 500 μM concentration in both contactors of the second line (noted MB5 and 6).

Figure 4:
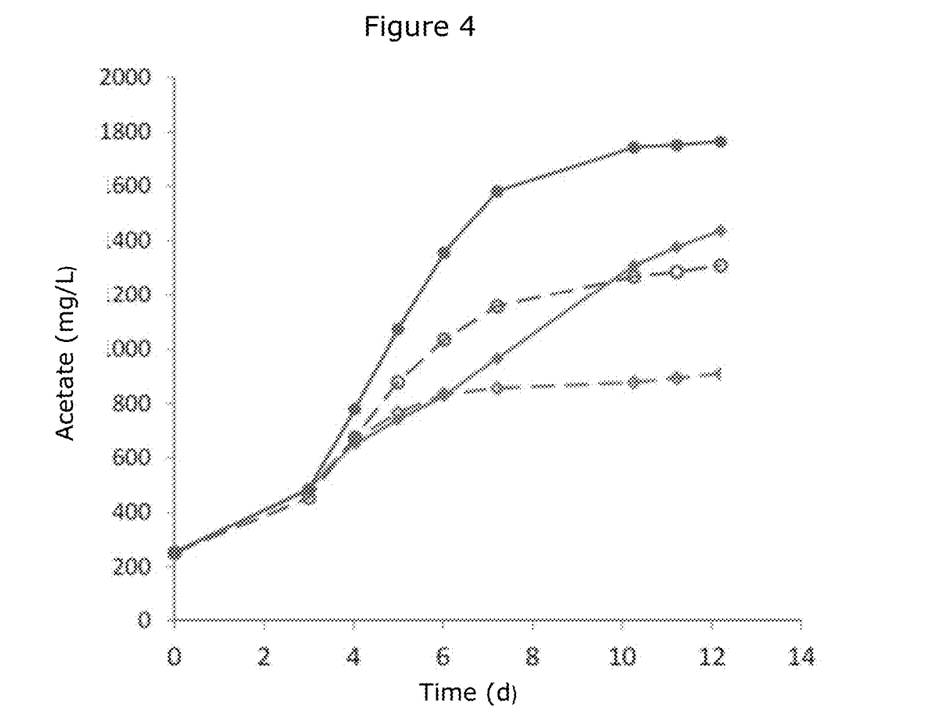
FIG. 4 represents the production of acetate for 12 days in contactors inoculated by sludge from wastewater purification plant (PP) and continuously fed by $N_2/CO_2/H_2$ (40/10/50 volume) in accordance with example 2. Said inoculated contactors are put either in the presence of a hydrogenation catalyst as a grid with a methanogenic inhibitor (●) or without a methanogenic inhibitor (◆), or in the absence of a hydrogenation catalyst with methanogenic inhibitor (○) or without a methanogenic inhibitor (◇).

The contactors of the first line (noted MB3 and 4) are reversed, that is the gas mixture first passes into the control contactor (MB) without a hydrogenation catalyst (◇, ○) with the contactor provided with the hydrogenation catalyst as a grid (◆, ●), in order to assess a possible effect of the order of the contactors.

A production of acetate is noted in all the contactors (FIG. 4). The presence of the methanogenic inhibitor (BES) actually inhibited the methanogenes, which explains the higher acetate concentrations on line MB5-6 in comparison with those of line MB 3-4. The concentrations obtained in 10 days are 1 250 mg·L$^{-1}$ for the control and 1 730 mg·L$^{-1}$ in the presence of a hydrogenation catalyst as a grid, namely a 38% improvement due to the presence of the catalyst.

The maximum production rate is 295 mg·L$^{-1}$·d$^{-1}$ and is stable over 3 days (between days 3 and 6) in the presence of grids, whereas it is 210 mg·L$^{-1}$·d$^{-1}$ and is only maintained over 2 days for the control. The same significant effect of the hydrogenation catalyst as a grid is observed in the absence of a methanogenic inhibitor, with less significant maximum concentrations.

The invention claimed is:

1. A process for synthesising organic molecules selected from the group consisting of formate, acetate and lactate comprising contacting, in an aqueous liquid medium under anaerobic conditions, at least one source of anaerobic microorganisms, capable of catalysing the reduction of carbon molecules by dihydrogen, with at least one dihydrogen stream, in the presence of at least one carbon source and at least one solid catalyst, wherein the solid catalyst is a bulk or supported metal catalyst.

2. The process according to claim 1, wherein all or part of the dihydrogen stream comes from a microbial electrolysis comprising the oxidation of organic waste, and/or an anaerobic digestion of organic waste, and/or water electrolysis.

3. The process according to claim 1, wherein the at least one carbon source is
   a. either in gas form and chosen from carbon monoxide and carbon dioxide,
   b. or in solution and chosen from solutions comprising carbonate, C$_1$-C$_8$ carboxylates, sugars, lactate, alone or in mixture.

4. The process according to claim 1, wherein the at least one solid catalyst is an electrically conducting or semiconductor catalyst.

5. The process according to claim 1, wherein the at least one solid catalyst is chosen from a hydrogenation catalyst or a catalyst comprising carbon materials, or a mixture thereof.

6. The process according to claim 1, wherein said metal catalyst comprises at least one metal chosen from iron, ruthenium, cobalt, nickel, chromium, platinum, palladium, rhodium, or a mixture of the same or of their oxides.

7. The process according to claim 6, wherein said metal catalyst is selected from the group consisting of iron, cobalt, nickel and ruthenium.

8. The process according to claim 1, wherein the solid catalyst is in the form of a grid, a plate or a three-dimensional or porous structure.

9. The process according to claim 4, wherein said catalyst is a metal membrane.

10. The process according to claim 1, wherein the solid catalyst is used as a support for the at least one source of microorganisms.

11. The process according to claim 1, wherein the source of microorganisms is chosen from the group comprising pure cultures, co-cultures, environmental inocula and complex microbial consortia.

12. The process according to claim 2, wherein the at least one carbon source is
   a. either in gas form and chosen from carbon monoxide and carbon dioxide,
   b. or in solution and chosen from solutions comprising carbonate, C$_1$-C$_8$ carboxylates, sugars, lactate, alone or in mixture.

13. The process according to claim 2, wherein the at least one solid catalyst is an electrically conducting or semiconductor catalyst.

14. The process according to claim 3, wherein the at least one solid catalyst is an electrically conducting or semiconductor catalyst.

15. The process according to claim 2, wherein the at least one solid catalyst is chosen from a hydrogenation catalyst or a catalyst comprising carbon materials, or a mixture thereof.

16. The process according to claim 3, wherein the at least one solid catalyst is chosen from a hydrogenation catalyst or a catalyst comprising carbon materials, or a mixture thereof.

17. The process according to claim 4, wherein the at least one solid catalyst is chosen from a hydrogenation catalyst or a catalyst comprising carbon materials, or a mixture thereof.

18. The process according to claim 6, wherein said metal catalyst comprises iron.

* * * * *